United States Patent
Ren et al.

(10) Patent No.: US 12,071,602 B2
(45) Date of Patent: Aug. 27, 2024

(54) INDUCTIVELY COUPLED CAPACITOR WIRELESS SENSOR SYSTEM FOR RAPID ANTIMICROBIAL SUSCEPTIBILITY TESTING

(71) Applicants: Dacheng Ren, Manlius, NY (US); Yikang Xu, Syracuse, NY (US)

(72) Inventors: Dacheng Ren, Manlius, NY (US); Yikang Xu, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 126 days.

(21) Appl. No.: 17/972,618

(22) Filed: Oct. 25, 2022

(65) Prior Publication Data

US 2023/0137251 A1 May 4, 2023

Related U.S. Application Data

(60) Provisional application No. 63/274,663, filed on Nov. 2, 2021.

(51) Int. Cl.
*G01N 35/02* (2006.01)
*C12M 1/34* (2006.01)
*C12Q 1/18* (2006.01)

(52) U.S. Cl.
CPC ............ *C12M 1/3407* (2013.01); *C12M 1/34* (2013.01); *C12Q 1/18* (2013.01); *G01N 35/028* (2013.01)

(58) Field of Classification Search
CPC ......... C12M 1/3407; C12M 1/34; C12Q 1/18; G01N 35/028; G01N 33/48707
See application file for complete search history.

(56) References Cited

U.S. PATENT DOCUMENTS

| | | | | |
|---|---|---|---|---|
| 6,649,402 B2* | 11/2003 | Van der Weide | ...... | C12M 41/36 435/305.3 |
| 2010/0266688 A1* | 10/2010 | Yang | ...................... | A61K 33/38 424/618 |
| 2018/0335405 A1* | 11/2018 | Shih | ..................... | G01N 29/036 |
| 2019/0136290 A1* | 5/2019 | Knopfmacher | .... | G01N 27/3275 |
| 2021/0262003 A1* | 8/2021 | Knopfmacher | .... | G01N 27/4148 |

* cited by examiner

*Primary Examiner* — Alvaro E Fortich
(74) *Attorney, Agent, or Firm* — David L. Nocilly; Bond Schoeneck & King PLLC

(57) ABSTRACT

An electrochemical biosensor based on magnetically coupled LC sensors for the rapid detection of microbial growth and sensitivity to microbials. The engineered LC sensors can be placed in 96 well plates and communicate the reading remotely with a receiver coil for signal analysis. The sensors were validated by testing the growth of *Escherichia. coli, Staphylococcus. aureus*, and *Pseudomonas aeruginosa* in the presence and absence of different antibiotics. Drug-resistant strains were used as controls. Bacterial growth was detected within 30 mins of culture inoculation, allowing rapid determination of antibiotic susceptibility at the phenotypic level. The pattern shown in the LC sensor AST is consistent with results collected with traditional optical density (OD) 600 nm measurement, additional validation was also performed with lysogeny broth (LB) dosed with fetal bovine serum (FBS). With the compatibility with 96-well plates, this rapid AST may be used for low-cost, point-of-care applications.

20 Claims, 22 Drawing Sheets

INDUCTIVELY COUPLED CAPACITOR WIRELESS SENSOR SYSTEM FOR RAPID ANTIMICROBIAL SUSCEPTIBILITY TESTING

CROSS-REFERENCE TO RELATED APPLICATIONS

The present application claims priority to U.S. Provisional Application No. 63/274,663, filed on Nov. 2, 2021.

BACKGROUND OF THE INVENTION

1. Field of the Invention

The present invention related to biological sensors and, more specifically, to a wireless sensor for detecting the susceptibility of microorganisms to antibiotics.

2. Description of the Related Art

Drug resistant infections present great challenges, especially in hospital settings where 30% of ICU patients are affected in high-income countries alone and two to three folds higher in low- and mid-income countries. According to a recent WHO report, 2.8 million AMR infections occur each year in the U.S. alone; and at least 1.27 million people died from AMR infection in 2019 worldwide. It is predicted that by 2050, there could be 10 million deaths a year globally if no effective treatment of AMR is available. Rapid detection of AMR has been proven critical for saving sepsis patients. In an animal study that mimics sepsis, it was revealed that antibiotic treatment administered 12 hours after bacterial inoculation resulted in a 96-hour survival rate of 80%, whereas treatment administered at 15 hours had the survival rate down to only 13.3%.

Current methods of pathogen detection by blood culture have a median growth time of around 13 hours. Without rapid detection of antimicrobial susceptibility, the patients may be given rather ineffective treatment. This can cause the precious window to prevent patient mortality to be missed due to AMR. Traditional phenotypic method such as dilution methods, agar disk diffusion testing, and gradient diffusion methods, typically takes 1-2 days to generate reliable results. Genotypic ASTs on the other hand, directly detect biomarkers associated with resistance with molecular detection tools including qPCR, whole-genome sequencing, and MALDI-TOF. Such tools are highly sensitive and could produce a report in hours. How-ever, these genomic approaches require detailed knowledge of AMR gene sequences and data analysis in advance, and thus cannot detect newly developed resistance mechanisms 6. Other new approaches are being developed including optical imaging to identify microbial in microfluidic device, pH sensor for tracking byproducts of microbial growth, bioluminescent assay of ATP, magnetic sensor with antibody coating, and electrochemical biosensors with peptide or anti-body coating. However, these methods require extensive image/data processing, complex sample preparation, and/or large equipment that is difficult to operate in clinical settings. Rapid high-throughput phenotypic ASTs are urgently needed to reduce sepsis mortality and help with the antibiotic stewardship programs.

Application of the LC sensor in medical devices dates back to 1967. The magnetic coupling between sensor coil and the detection coil transmits AC electricity to the sensor circuit where the resonant frequency of the inductor (L) and capacitor (C) could be interpreted by analyzing the resonant frequency of the system on a frequency spectrum. The resonant frequency changes in response to the surrounding environment, allowing the detection of substances that change the surface property of the sensor. The wireless nature of the sensor enables sensing in hard-to-access locations either in an instrument or the human body such as a wound health sensor. In addition, LC sensor requires no integrated power to operate. Thus, it is possible to make small form factor LC sensors with long life span. These advantages make LC sensors attractive in designing biomedical devices where the sensors are often sealed and require low to no maintenance to operate in biological environments. However, this technology did not come onto the main stage of remote query systems until the development of Micro Electro-Mechanical System (MEMS).

BRIEF SUMMARY OF THE INVENTION

The present invention provides a rapid phenotypic AST system based on a wirelessly magnetically coupled LC sensor that can exploit the capacitive nature of bacteria. The present invention thus bypasses the need for targeted sample enrichment surface modifications or coatings, in turn achieving bacterial growth monitoring or killing/inhibition behavioral study to aid in rapid diagnosis of bacterial infection and ASTs. A bacterial culture may be diluted and aliquoted into a well plate having a sensor according to the present invention. A receiver coil connected to an impedance analyzer on the bottom of the well plate wirelessly communicates with the sensor and scans a spectrum of electrical wavelength to find the resonance frequency between the sensor and the receiver coil. The resonance frequency of the system is recorded periodically and combined with the parameter of the sensor to calculate the permittivity of the bacteria culture. The permittivity readout is plotted as a time series, and the slope of the curve over an initial time period is used to access the sensitivity score of bacteria against specific antibiotics. The baseline of the sensitivity score is determined by acquiring the growth slope of sterile LB media with treatment and known sensitive strain under treatment.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 5:
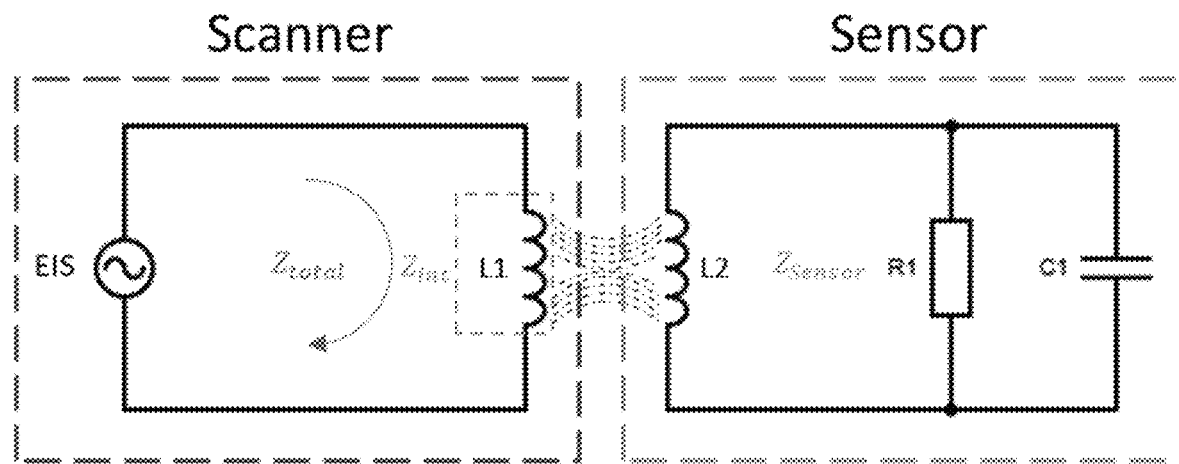

FIG. 5 is a schematic of a resonant circuit design for use with the present invention, where the inductors represent the coils and the parallel resistor R1 and capacitor C1 represents the IDC on the sensor side, with $Z_{sensor}$ representing the total impedance of the coil and the IDC. At the scanner side, $Z_{int}$ is the intrinsic impedance of the coil, $Z_{total}$ is the total measured impedance of the coil, and a signal generator/analyzer.

Figure 6:
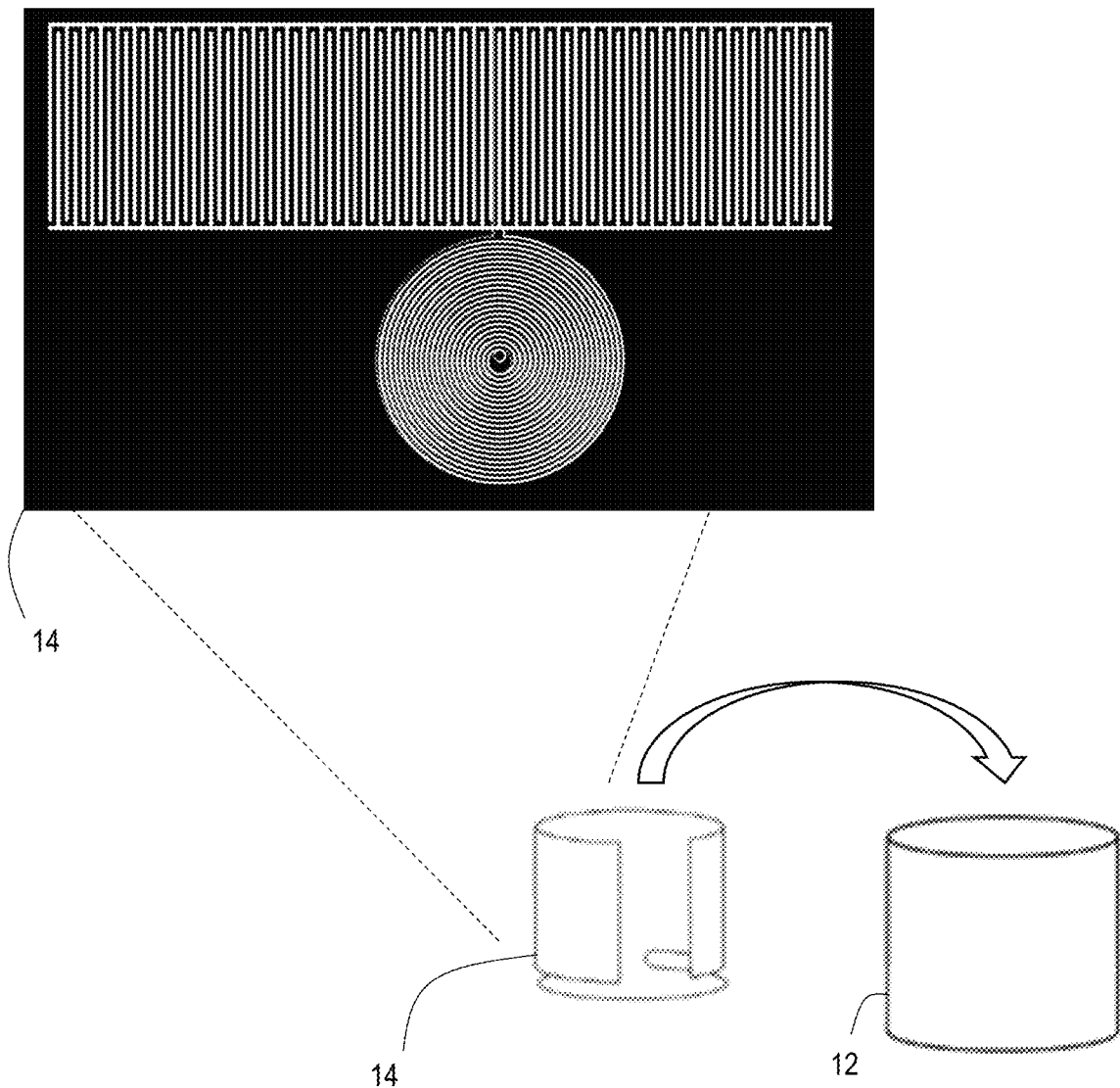

FIG. 6 is a schematic of the experimental setup showing a close up of the coated sensor as well as the finished sensor and exemplary well from a 96 well plate assembly.

Figure 7:
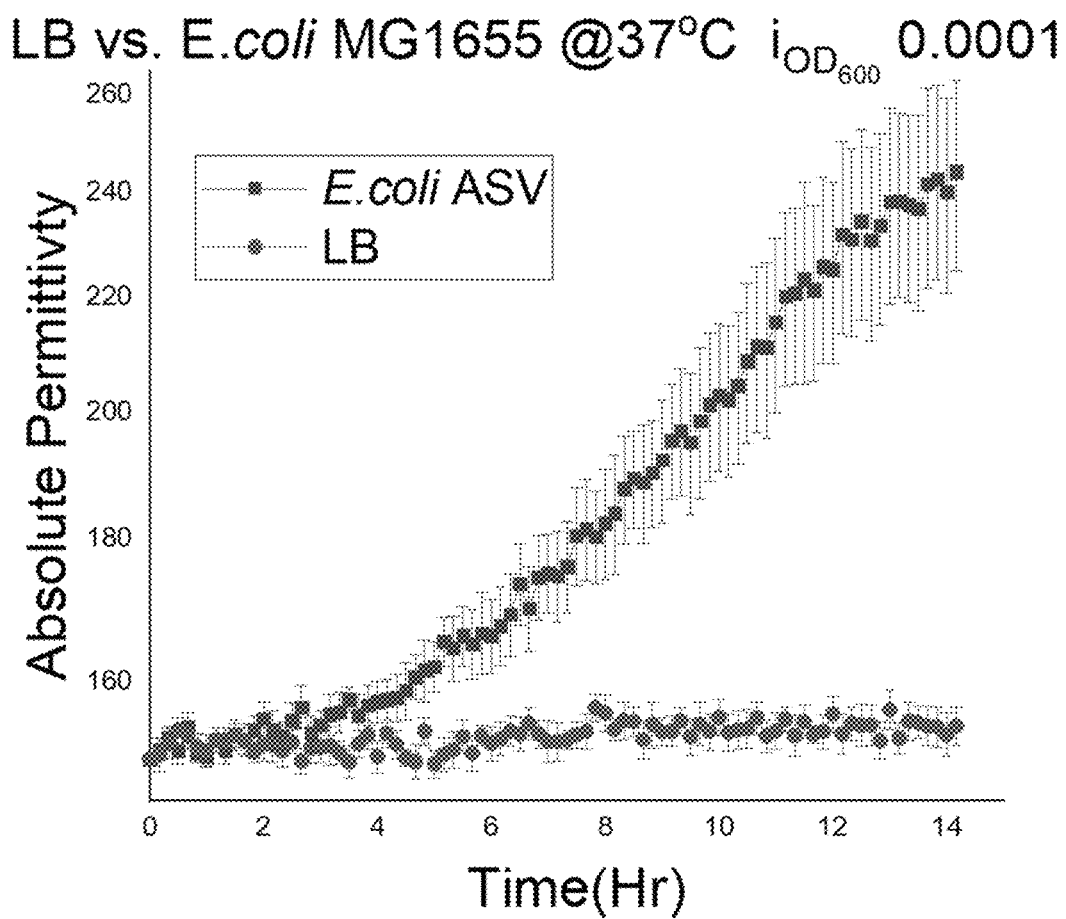

FIG. 7 is a graph of the overnight growth curve of *E. coli* MG1655 ASV strain obtained with initial sensor design.

Figure 8:
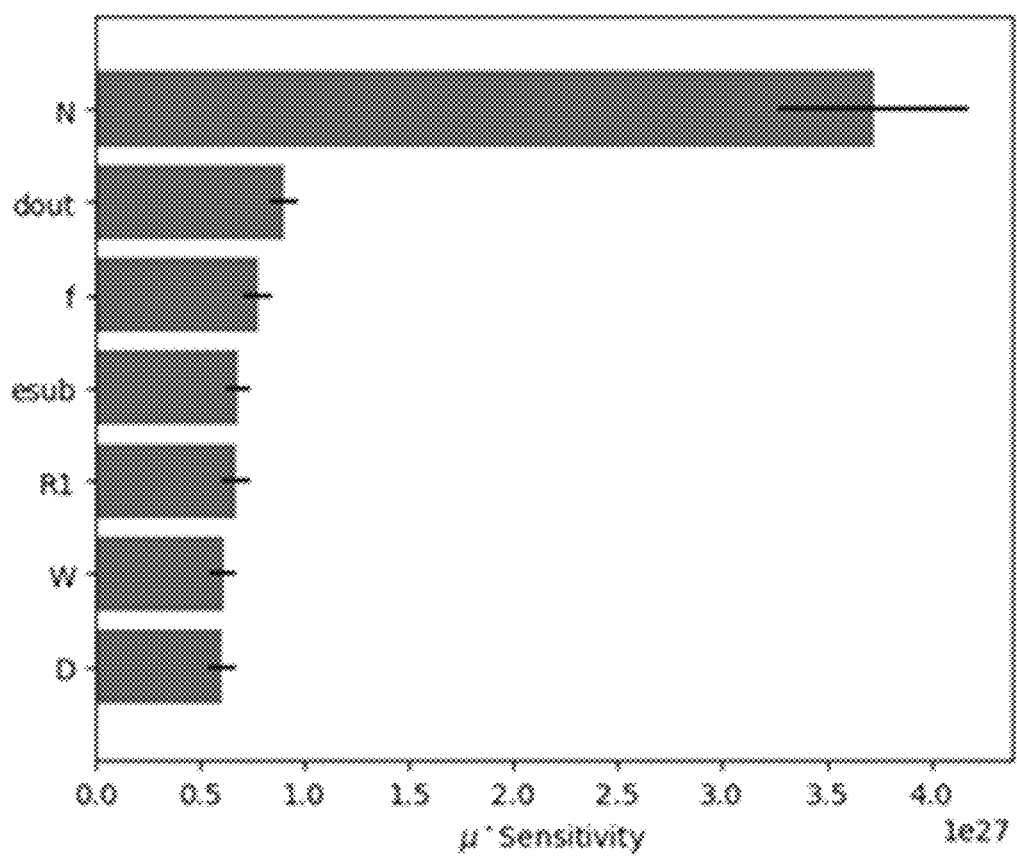

FIG. 8 is a bar chart of the method of Morris multivariable sensitivity analysis of Equation 5 where $d_{out}$ is the outer diameter of the sensor.

Figure 9:
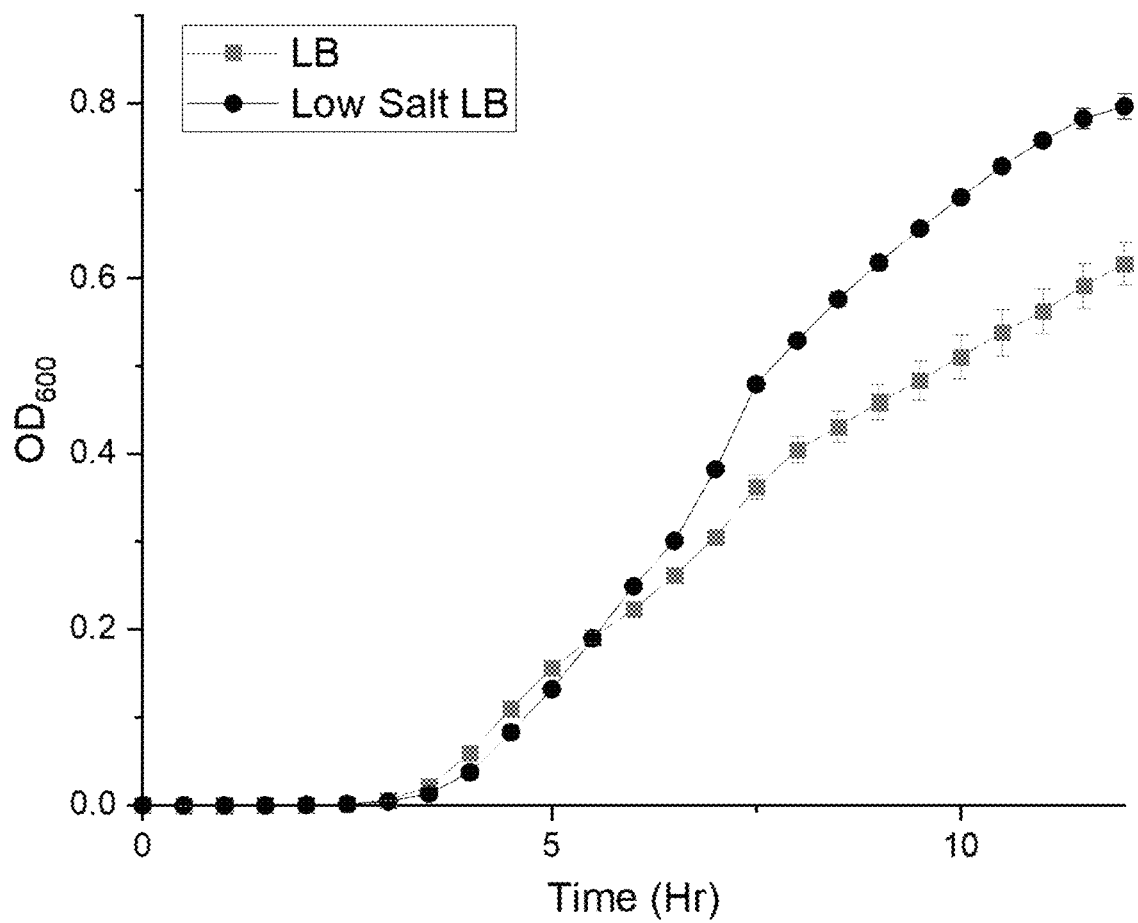

FIG. 9 is a graph of a growth curve of *E. coli* MG1655 in LB and low salt LB measured by traditional $OD_{600}$ method on a Biotek Epoch2 microplate spectrophotometer over 12 hours with 15 mins interval.

Figure 10:
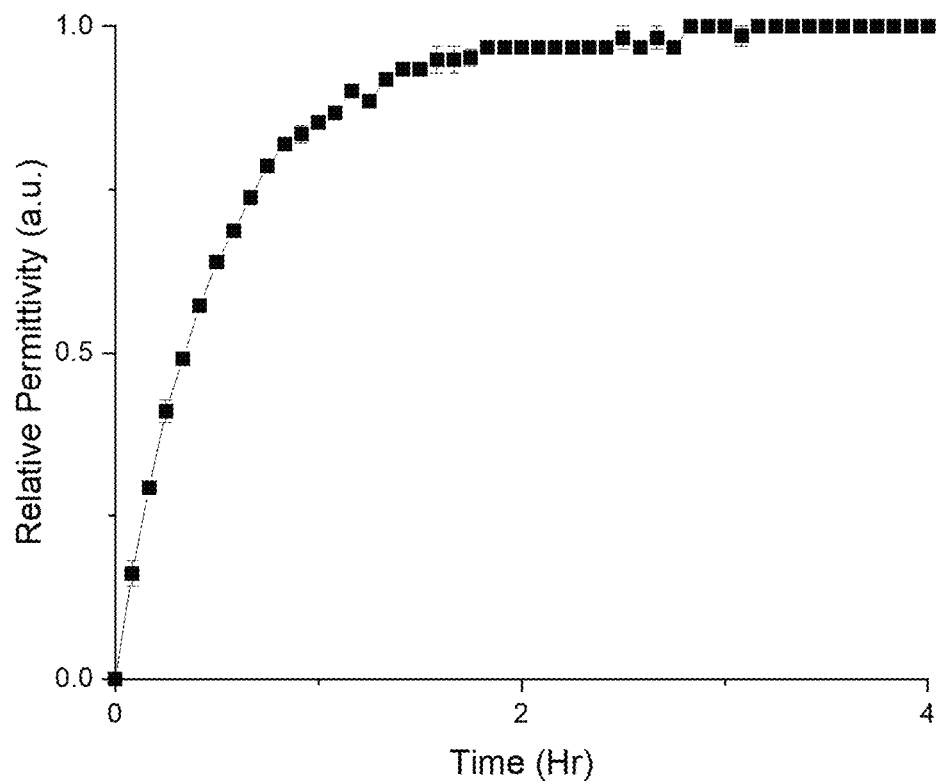

FIG. 10 is a growth curve of *E. coli* MG1655 in low salt LB measured in the sensor system over 4 hours with 5 mins interval.

Figure 11:
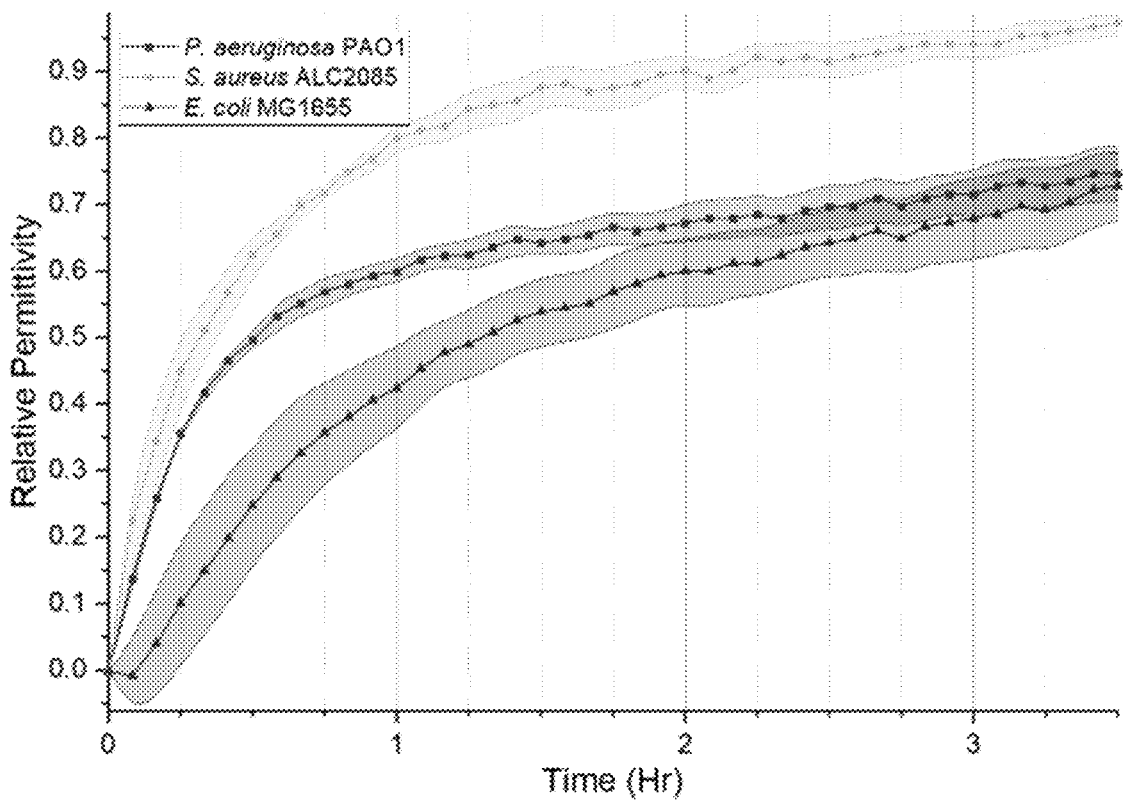

FIG. 11 shows growth curves of *E. coli* MG1655, *S. aureus* ALC2085, and *P. aeruginosa* PAO1 in the sensor system over 3.5 hours with 5 mins interval.

Figure 12:
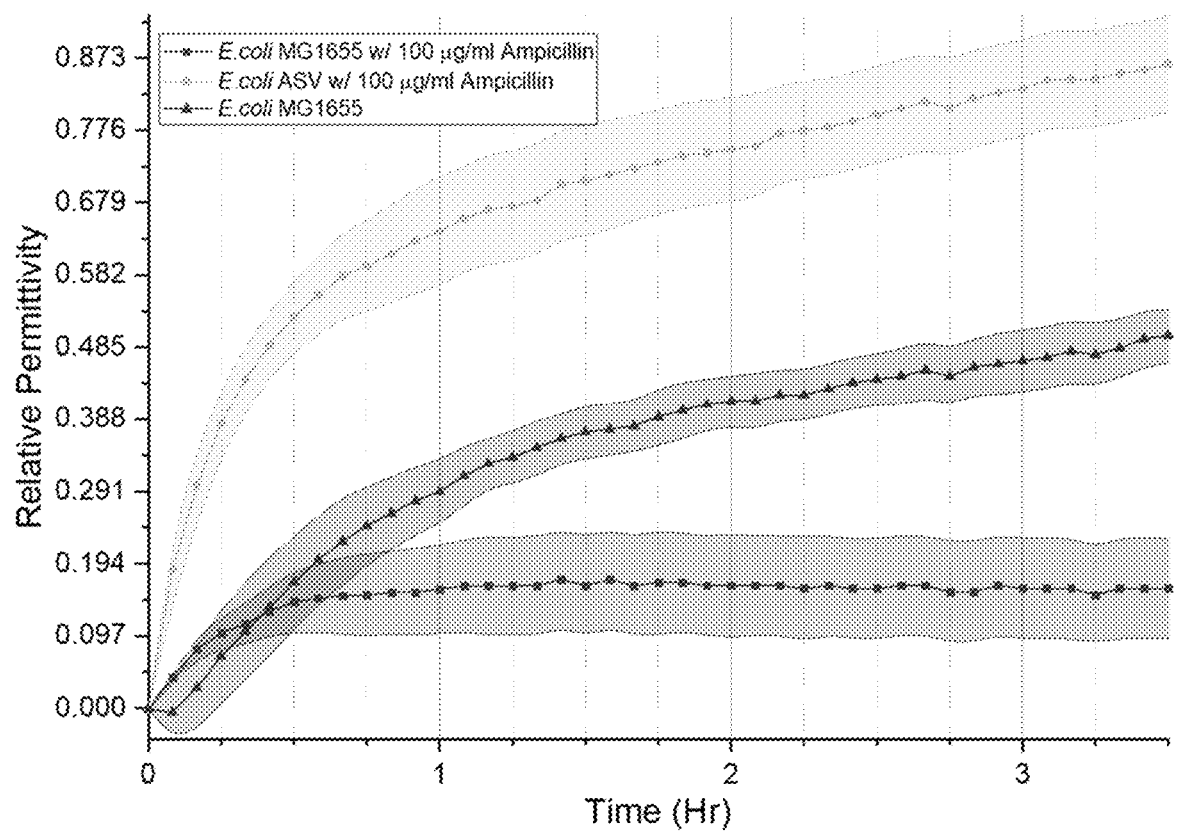

FIG. 12 shows growth curves of *E. coli* MG1655 and *E. coli* MG1655 ASV ampicillin resistant strain with and without 100 µg/mL ampicillin treatment.

Figure 13:
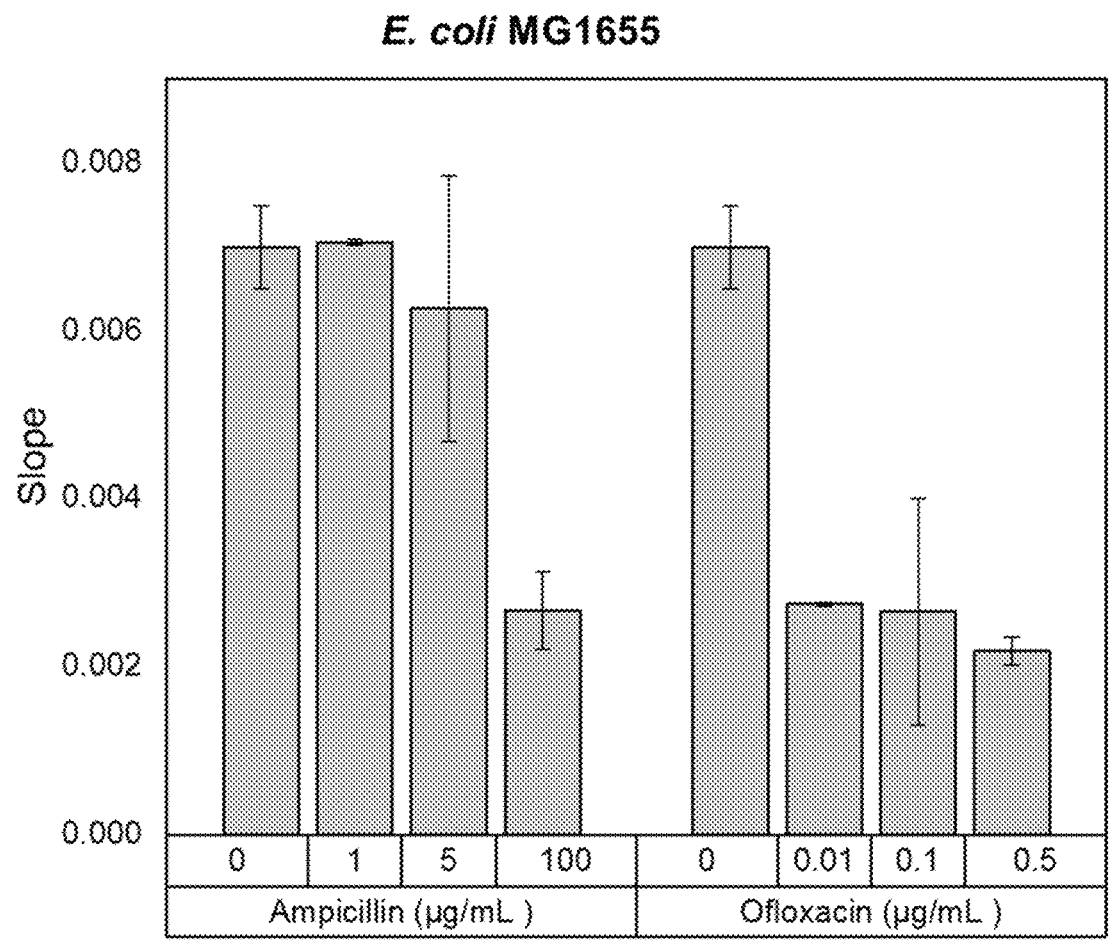

FIG. 13 is a bar chart of the slopes of permittivity curves with ampicillin and ofloxacin treatment on *E. coli* MG1655 WT and untreated control.

Figure 14:
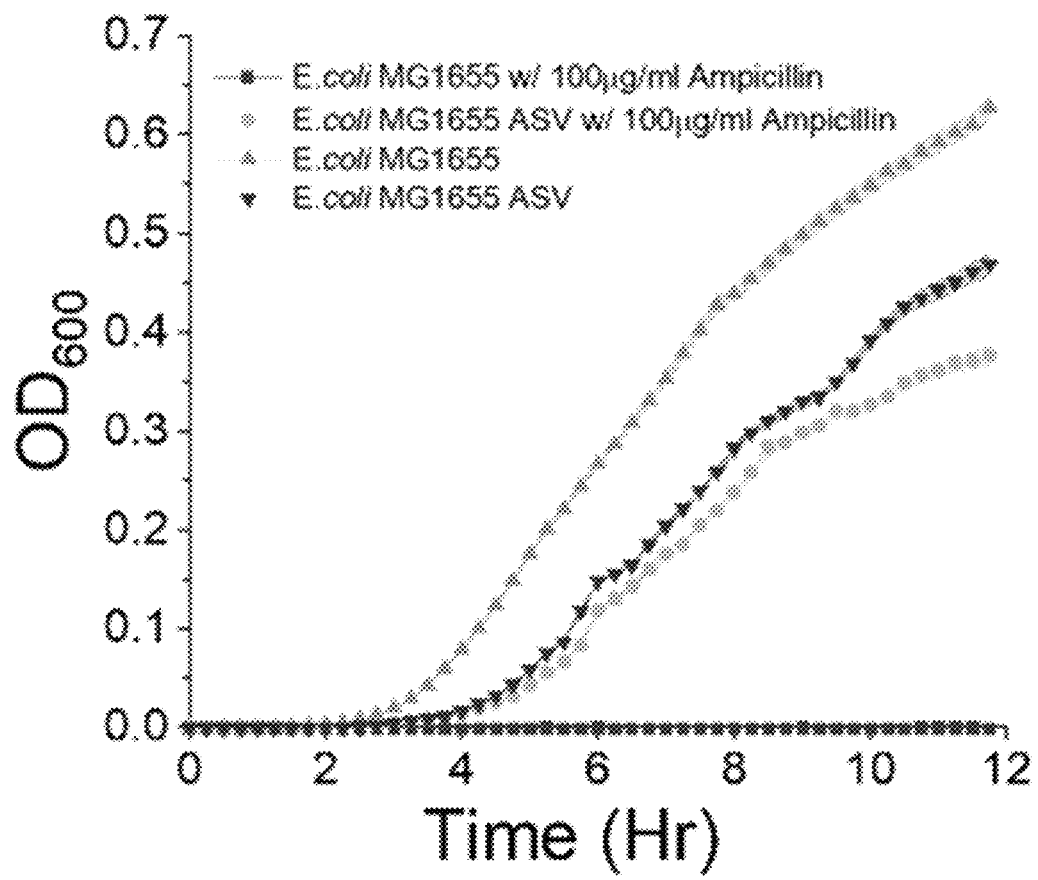

FIG. 14 is a graph of the $OD_{600}$ measurement of *E. coli* MG1655 WT dose dependent response toward ampicillin.

Figure 15:
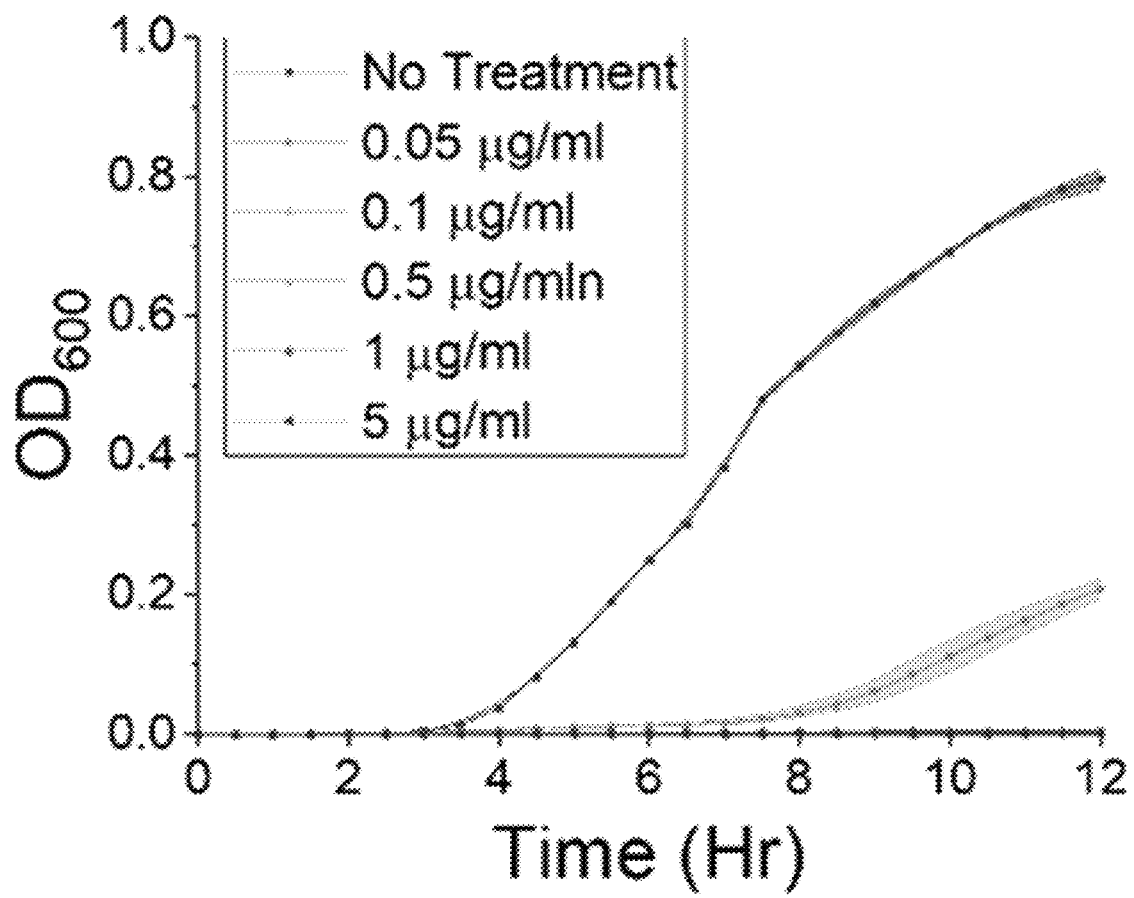

FIG. 15 is a graph of the $OD_{600}$ measurement of *E. coli* MG1655 WT dose dependent response toward ofloxacin.

Figure 16:
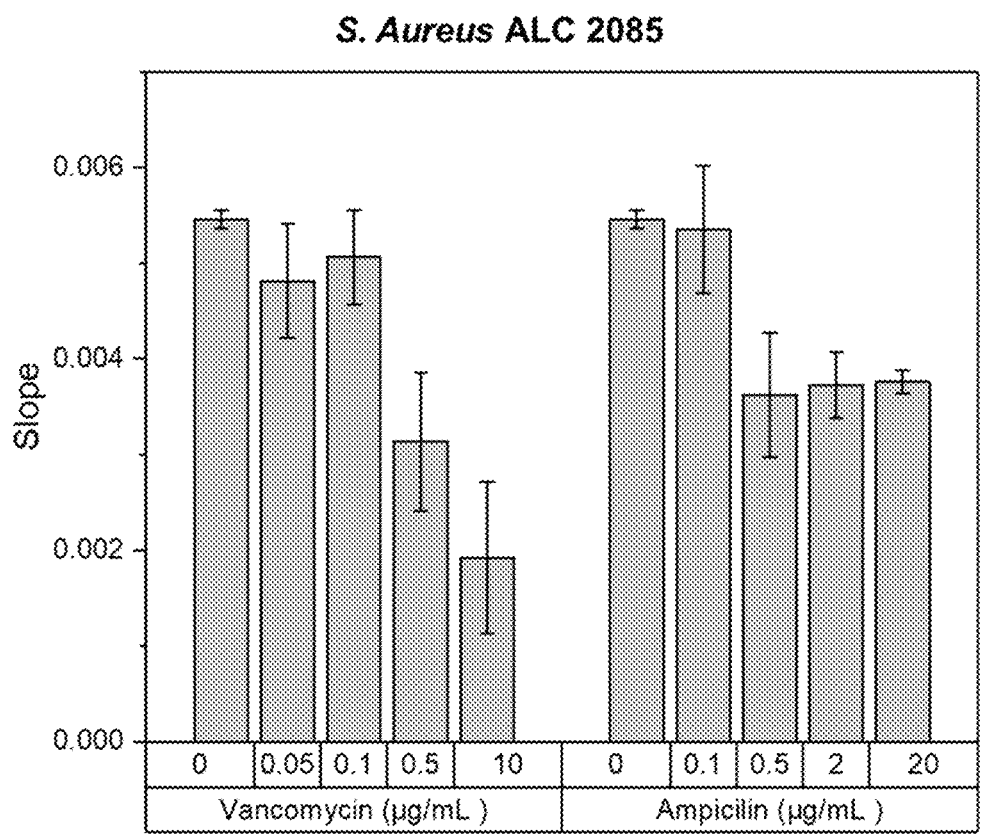

FIG. 16 is a bar chart of the slopes of permittivity curves with vancomycin and ampicillin treatment on *S. aureus* ALC2085.

Figure 17:
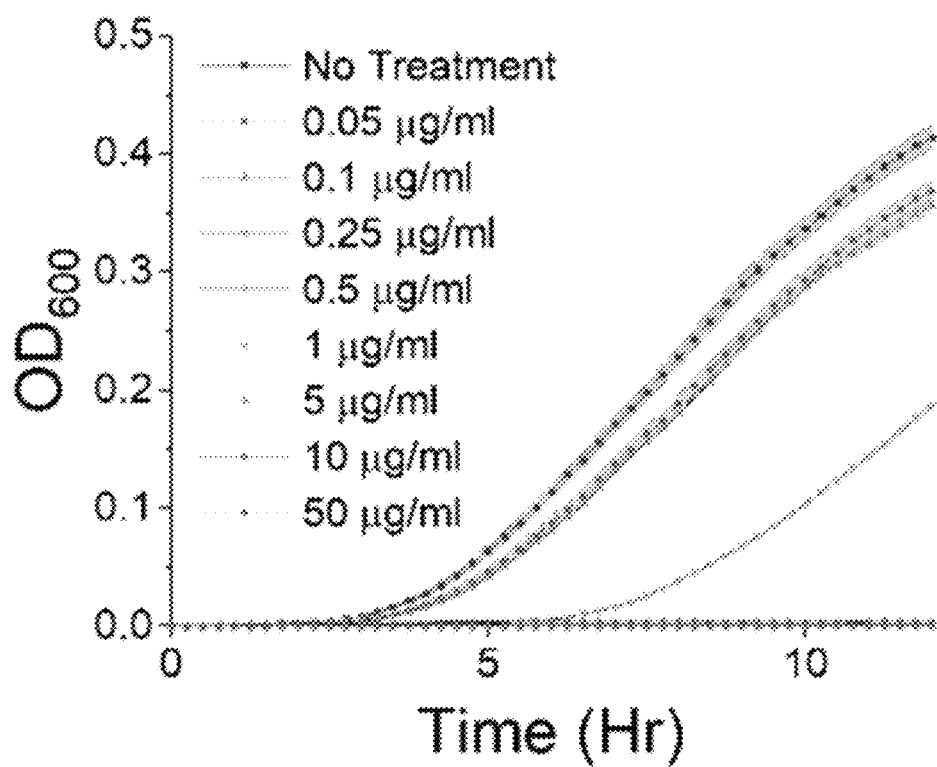

FIG. 17 is a graph of the $OD_{600}$ measurement of *S. aureus* ALC2085 dose dependent response toward vancomycin.

Figure 18:
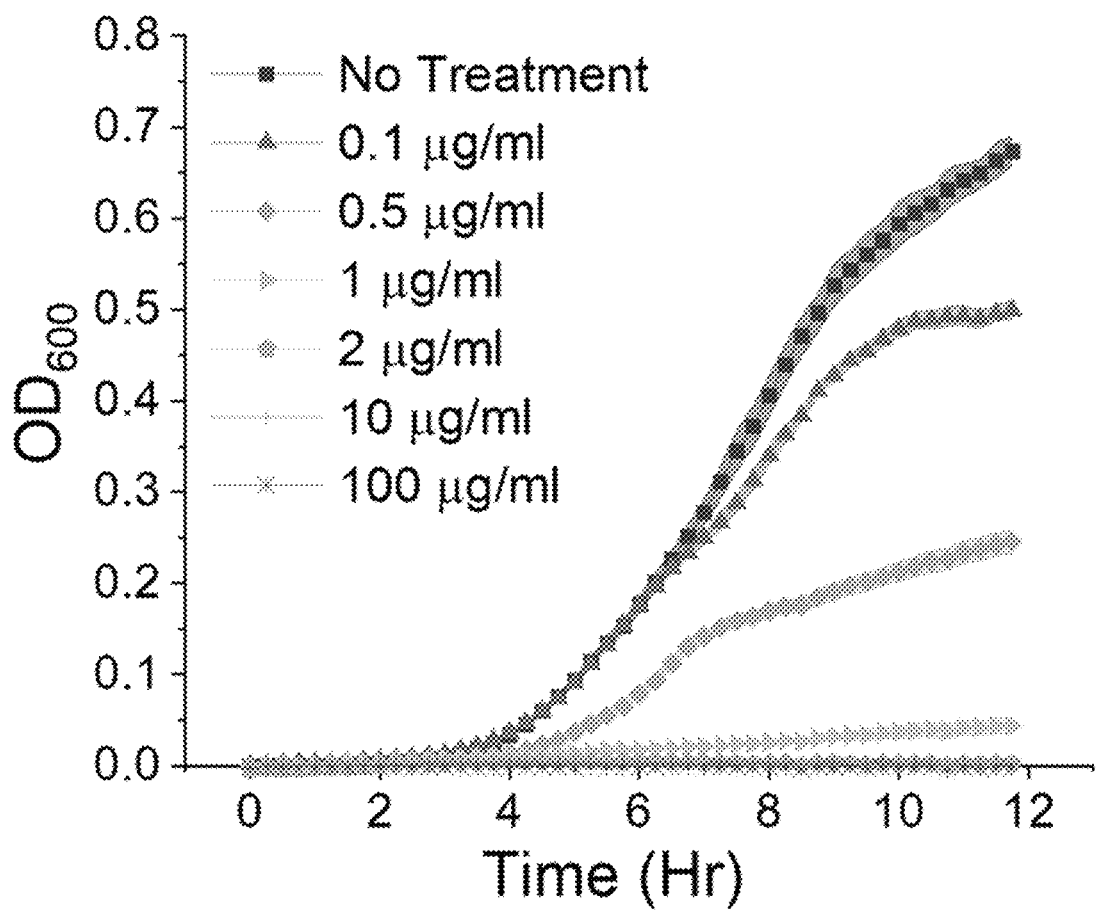

FIG. 18 is a graph of the $OD_{600}$ measurement of *S. aureus* ALC2085 dose dependent response toward ampicillin.

Figure 19:
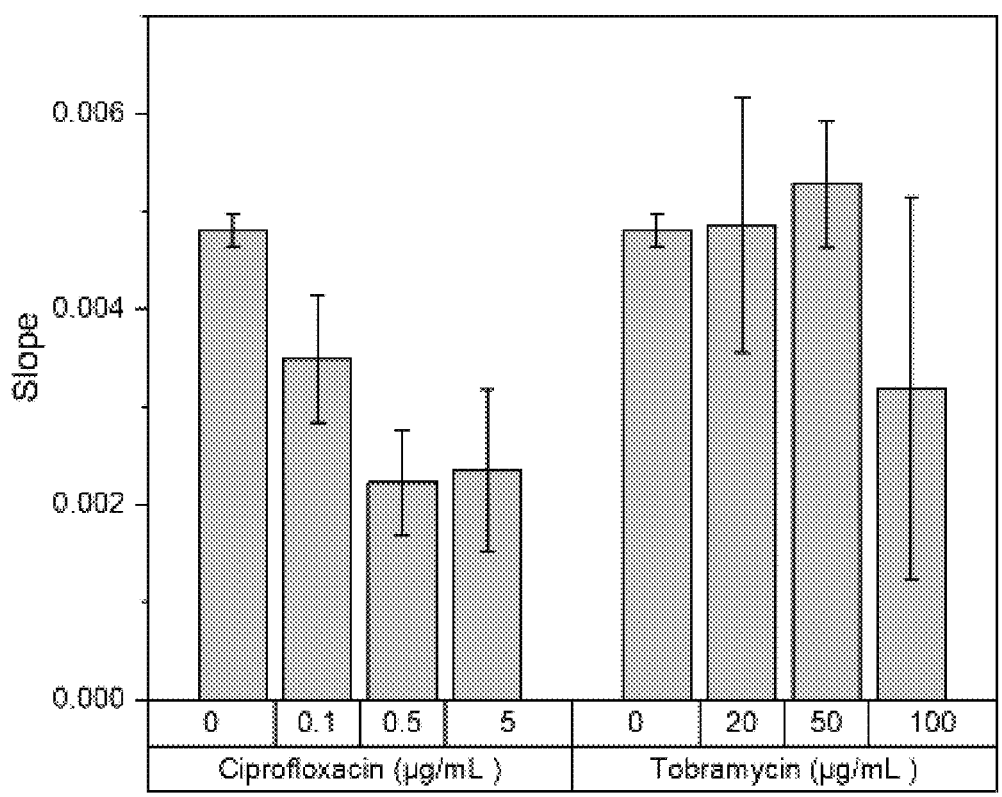

FIG. 19 is a bar chart of the slopes of ciprofloxacin and tobramycin treatment on *P. aeruginosa* PAO1.

Figure 20:
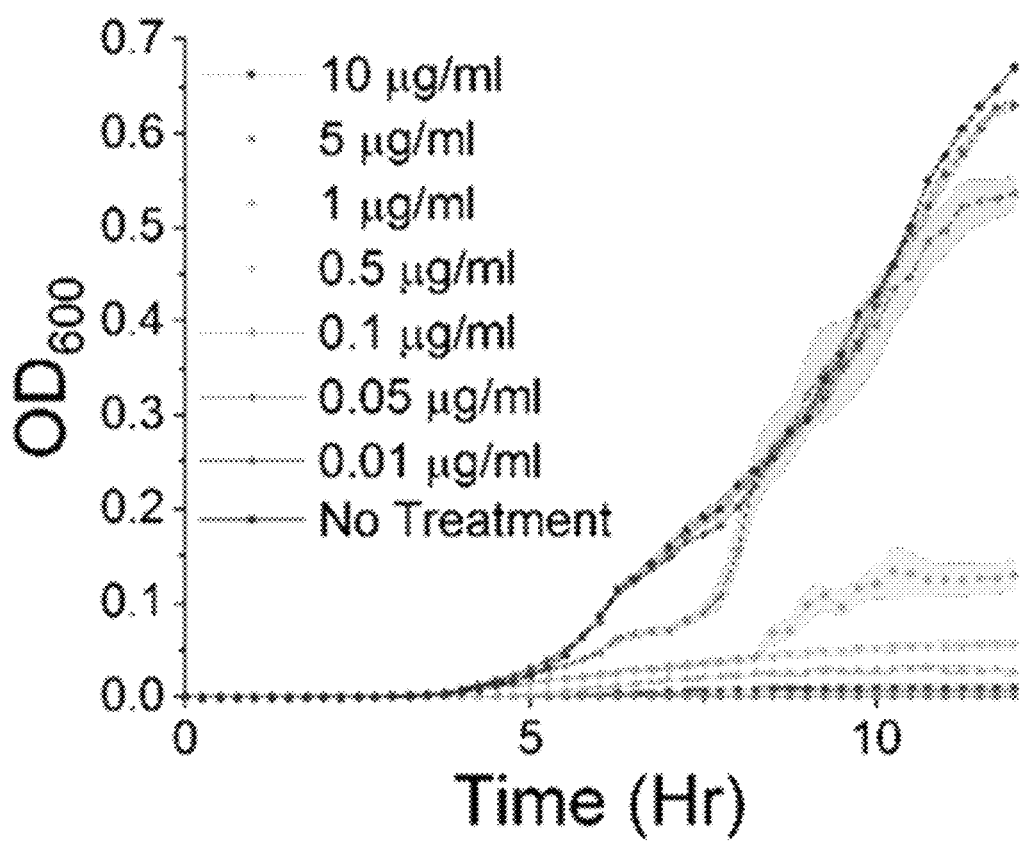

FIG. 20 is a graph of the $OD_{600}$ measurement of *P. aeruginosa* PAO1 dose dependent response toward ciprofloxacin.

Figure 21:
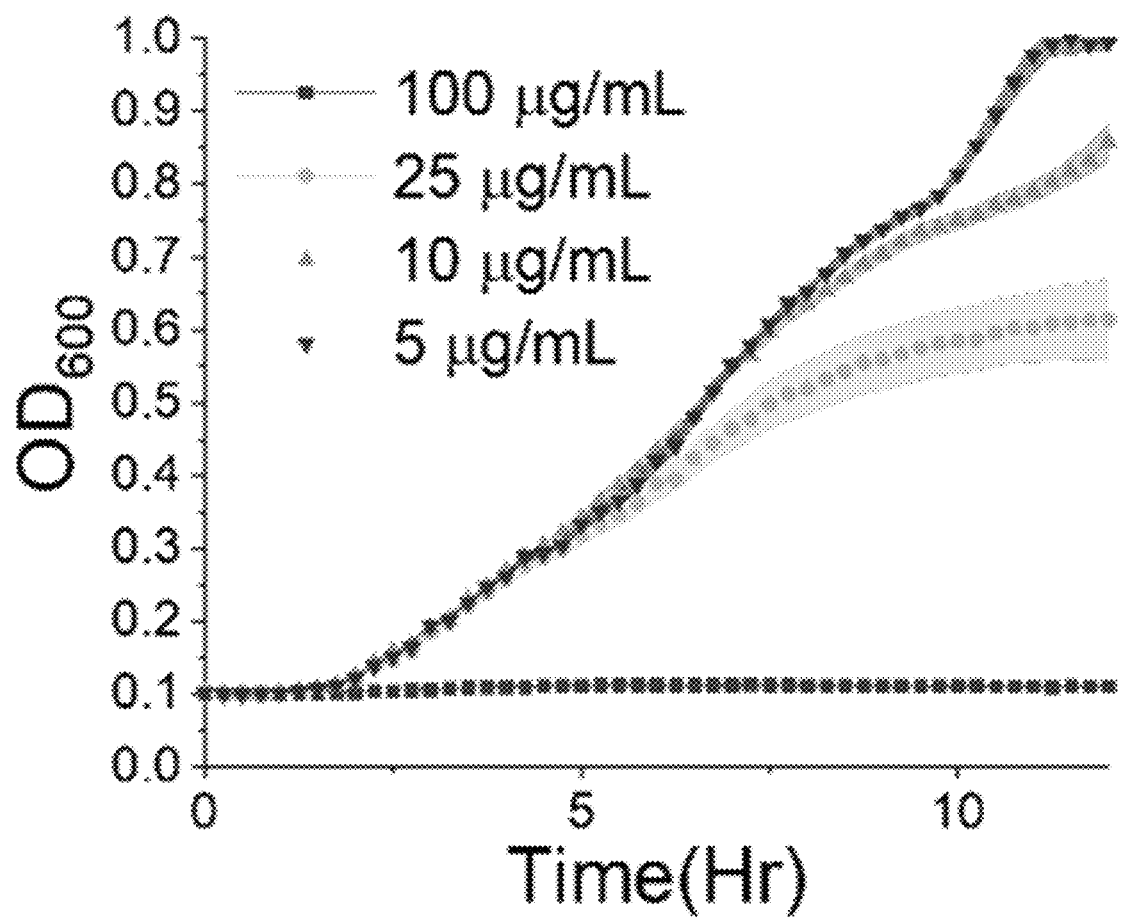

FIG. 21 is a graph of the $OD_{600}$ measurement of *P. aeruginosa* PAO1 dose dependent response toward tobramycin.

Figure 22:
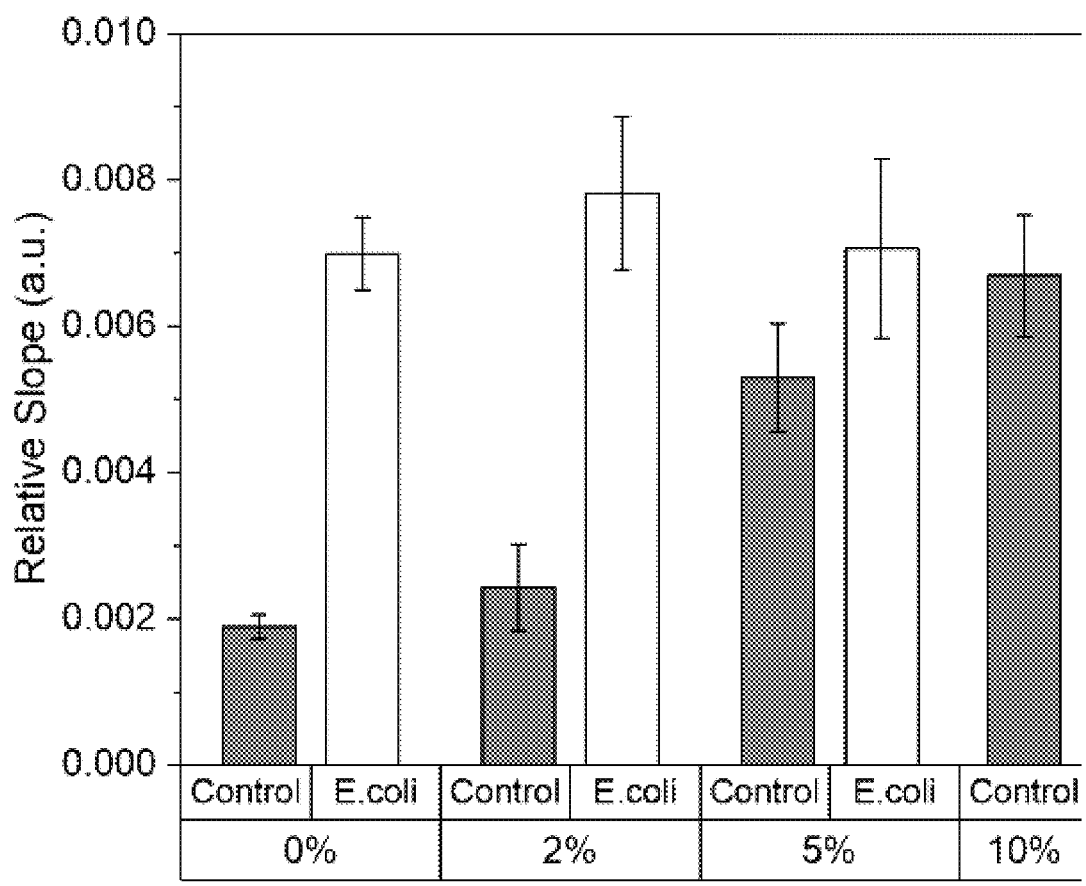

FIG. 22 is a bar chart of the slopes of FBS dosed low salt LB and that of *E. coli* MG1655 grown in FBS dosed low salt LB.

DETAILED DESCRIPTION OF THE INVENTION

Figure 1:
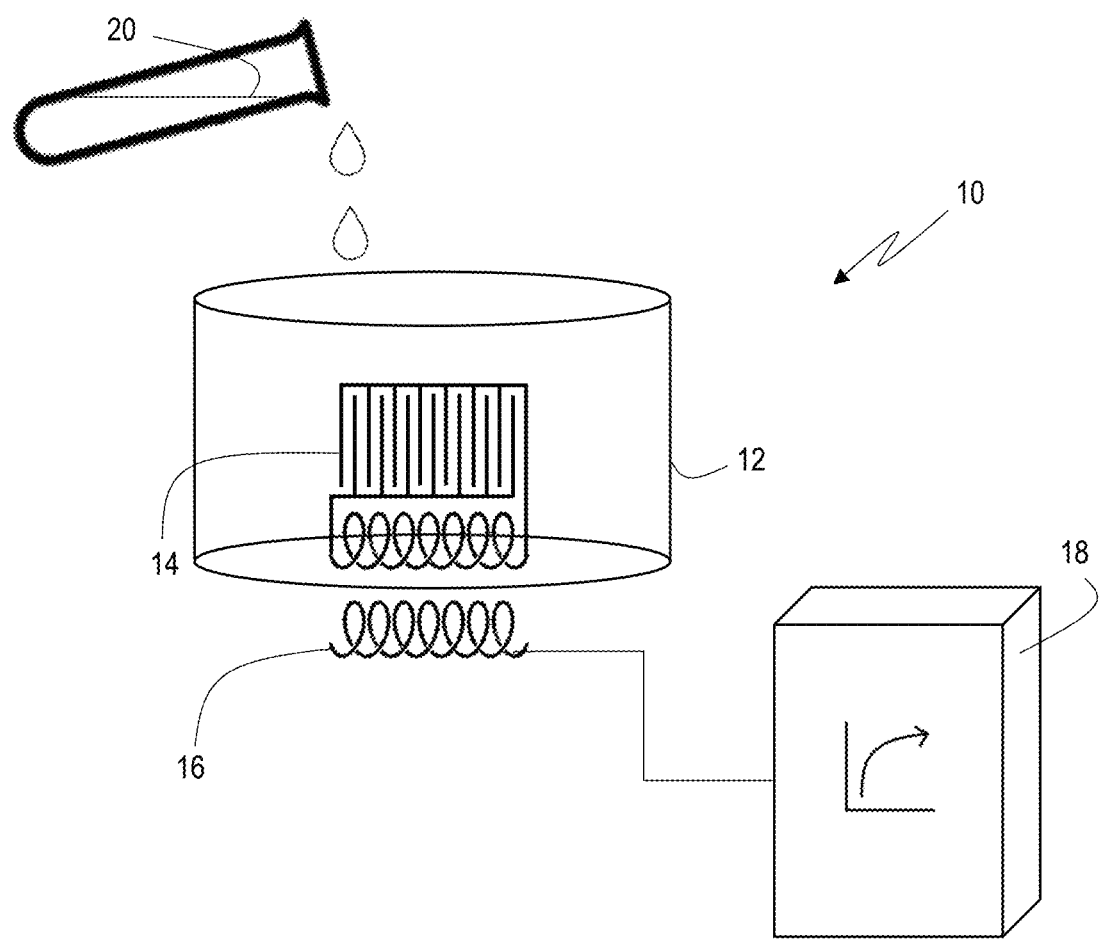
FIG. 1 is a schematic of a bacterial monitoring system according to the present invention where a diluted bacteria culture with desired antibiotic may be aliquoted into individual well on a well plate and a sensor in the well communicates wirelessly with an impedance analyzer.

Referring to the drawings, wherein like numeral refer to like parts throughout, there is seen in FIG. 1 a system 10 for bacterial treatment monitoring according to the present invention. System 10 includes a well plate 12 having a sensor 14 positioned therein. A receiver coil 16 is positioned on the bottom of well plate 12 and wirelessly coupled to the sensor 14. An impedance analyzer 18 is coupled to receiver coil 16 and configured to identify and record the resonance frequency of sensor 14 and receiver coil 16 over a first predetermined series of time periods. Impedance analyzer 18 is further configured to calculate the permittivity of a bacterial culture 20 placed in well plate 12. The permittivity is tracked over a second predetermined period of time and plotted so that the slope of the plot may be used to generate a sensitivity score representing the sensitivity of bacterial culture 20 to a given antibiotic added to well plate 12 at the outset. Well plate 16 may comprise a standard 96 well plate for simultaneous assessment of multiple populations, and impedance analyzer 18 may comprise a Keysight E4990A-20 impedance analyzer. The first predetermined series of time periods may comprise five minutes, while the second predetermined period of time may comprise 30 minutes. A baseline of the sensitivity score may be determined by acquiring the growth slope of sterile LB media with treatment and known sensitive strain under treatment. The system of the present invention may thus be provided at a low cost and does not requires any special sample handling. Samples can also be loaded into standardized test plates using automated workflow systems, with report generated within 30 minutes.

Example

Bacterial Media, Reagents and Materials

Low salt LB medium was prepared using 0.5 g/L NaCl, 10 g/L Tryptone, 5 g/L Yeast Extract, with additions of Fetal Bovine Serum. Antibiotics tested include ampicillin, ofloxacin, ciprofloxacin, vancomycin, and tobramycin. The sensors and the receiver plate were fabricated on a flexible Polyimide Flex circuit board (Custom ordered from PCBWay Prototype to volume production Factories, Shenzhen, China). Oil-based polyurethane protective spray coating was obtained from MINWAX. Permittivity data was measured using an impedance analyzer (E4990A-20 Keysight, Santa Rosa, CA).

Bacteria Samples Preparation

Overnight bacterial cultures were grown in 25 mL low salt LB medium and incubated at 37° C. for 16 hours with shaking at 200 rpm. To test antibiotic susceptibility, overnight cultures were used to inoculate in a low salt LB medium with starting $OD_{600}$ of 0.001. Three hundred µL of the inoculant was then aliquoted to a 96 well plate with LC sensor inserts and quickly transferred to a 30° C. culture room for growth tracking.

In order to calculate the complex permittivity of the bacterial culture, an equation can be derived from parameters of the LC sensor and the resonant frequencies collected from the impedance analyzer[19-21]:

$$\varepsilon = \frac{C_1}{k\varepsilon_0} - \varepsilon_{sub} + \frac{1}{kR_1\omega_{zero-inductance}\varepsilon_0} \quad (1)$$

In which k is the cell constant of the IDC[22] defined by:

$$k = \frac{L(N-1)k\left[1-\left(\frac{D}{D+W}\right)^2\right]^{\frac{1}{2}}}{2K\left[\frac{D}{D+W}\right]} \quad (2)$$

Figure 2:
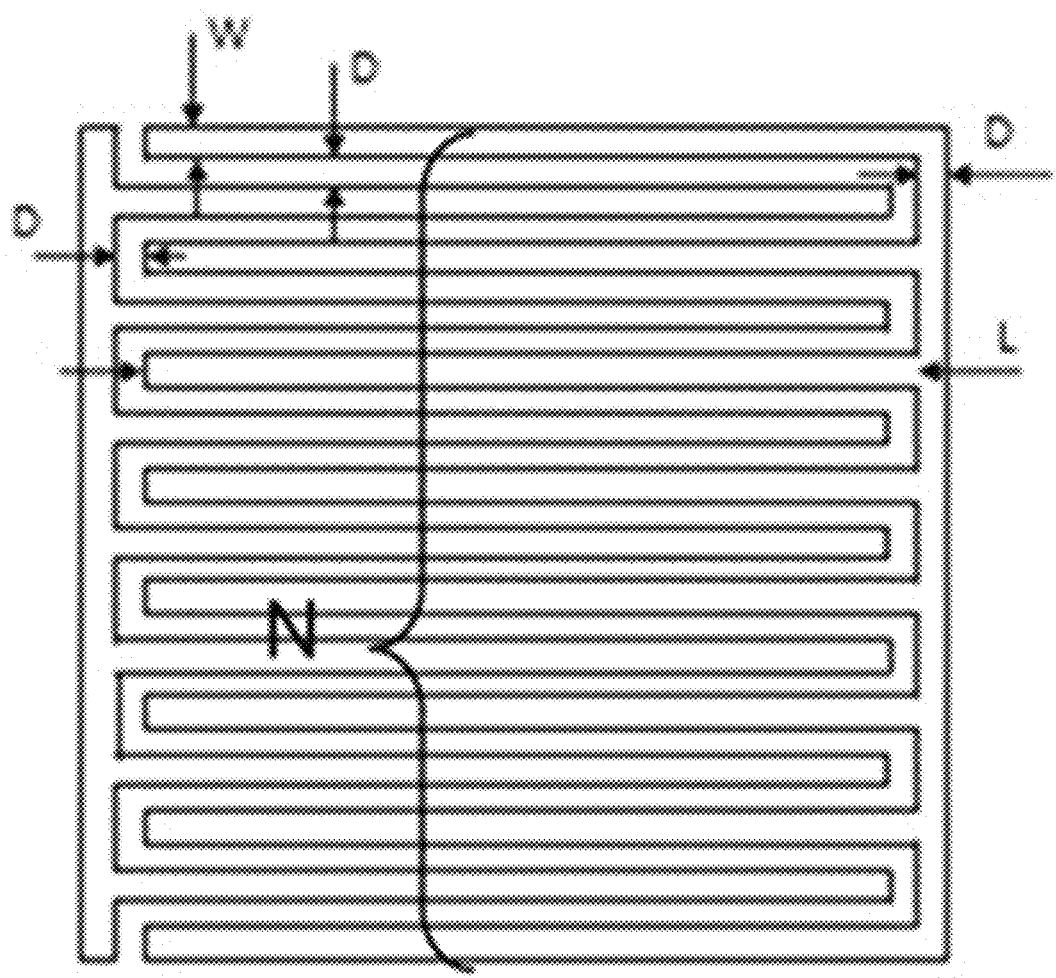
FIG. 2 is a schematic of exemplary IDC for use with the present invention along with its parameters, where N is the number of digits in total, L is the length of each digit, D is the gap between neighboring digits, and W is the width of the digits.

All parameters needed to calculate k can be found illustrated in FIG. 2, except for the elliptic integral of the first kind K[A]. Using the above permittivity equation, a permittivity vs time plot was generated. Thus, the permittivity changes in the system can be tracked, to monitor bacterial growth, allowing rapid detection of antibiotic susceptibility.

Signal Processing

The resonant circuit consists of two sides, including a circuit with a coil and an interdigitated capacitor (IDC) on the sensor side and a detection coil and a signal generator/analyzer on the scanner side, as seen in FIG. 5. Circuit analysis could be used to obtain the following equation from this circuit:

$$Z_{total} = Z_{int} + \frac{\omega^2 M^2}{Z_{sensor}} \quad (3)$$

In this equation, $Z_{int}$ is considered as background impedance of the system and is subtracted using the built-in function of the EIS, and $Z_{sensor}$ can be represented using the frequency domain as:

$$Z_{sensor} = j\omega L_2 + \frac{R_1}{1 + j\omega R_1 C_1} \quad (4)$$

Substituting equation (4) into equation (3), and combining with the subtraction of background noise mentioned above, the representation of total impedance on the scanner side becomes:

$$Z_{Scanner} = \frac{\omega^2 M^2 R_1}{(R_1 - \omega^2 R_1 C_1 L_2)^2 + \omega^2 L_2^2} + j\frac{\omega^2 M^2(\omega R_1 C_1(R_1 - \omega^2 R_1 C_1 L_2) - \omega L_2)}{(R_1 - \omega^2 R_1 C_1 L_2)^2 + \omega^2 L_2^2} \quad (5)$$

It is important to note that in this equation, ω (frequency), M (mutual inductance), and $L_2$ (inductance of sensor coil) are all known parameters and can be controlled either by changing the input or the design of the IDC. This means only two parameters, the $R_1$ and $C_1$ are unknown and can be solved by using equation 5 after setting the imaginary part of the impedance to 0 at the zero-reactance frequency (Eq. 6) and taking the derivative of the real part of the equation (3) to set ω to resonant frequency (Eq. 7).

$$\omega_{zero\text{-}inductance} = \sqrt{\frac{1}{LC} - \frac{1}{R^2 C^2}} \quad (6)$$

$$\omega_{resonant} = \sqrt{\frac{1}{LC}} \quad (7)$$

With these two frequencies calculated, the complex permittivity of the IDC can be calculated with the two equations mentioned above (Eq. 1 & 2).

Electromagnetic Coupling Analysis of the Sensor

Figure 3:
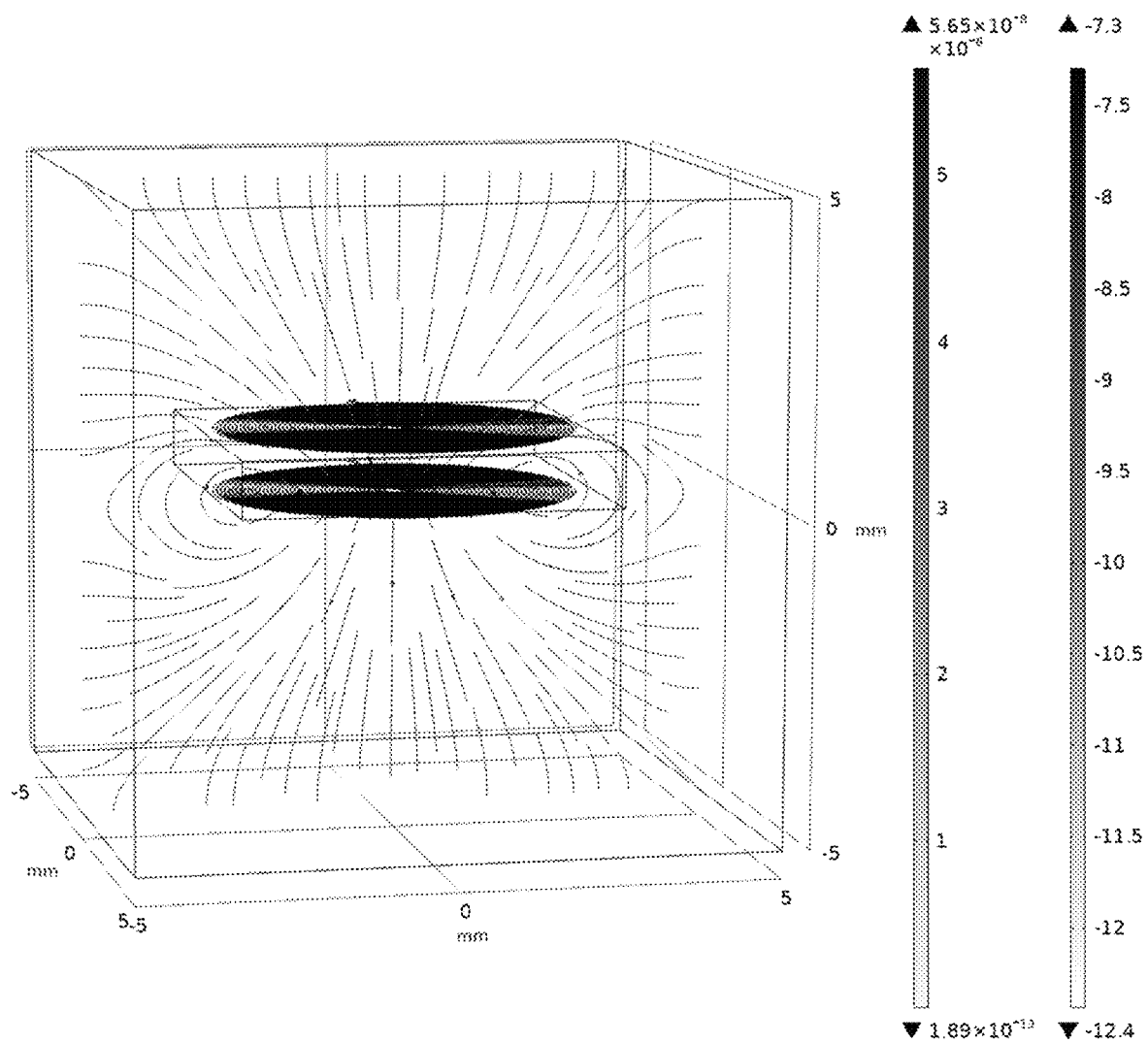
FIG. 3 is a COMSOL simulation of magnetic coupling between the receiver coil and the sensor coil across a piece of polystyrene plastic.
Figure 4:
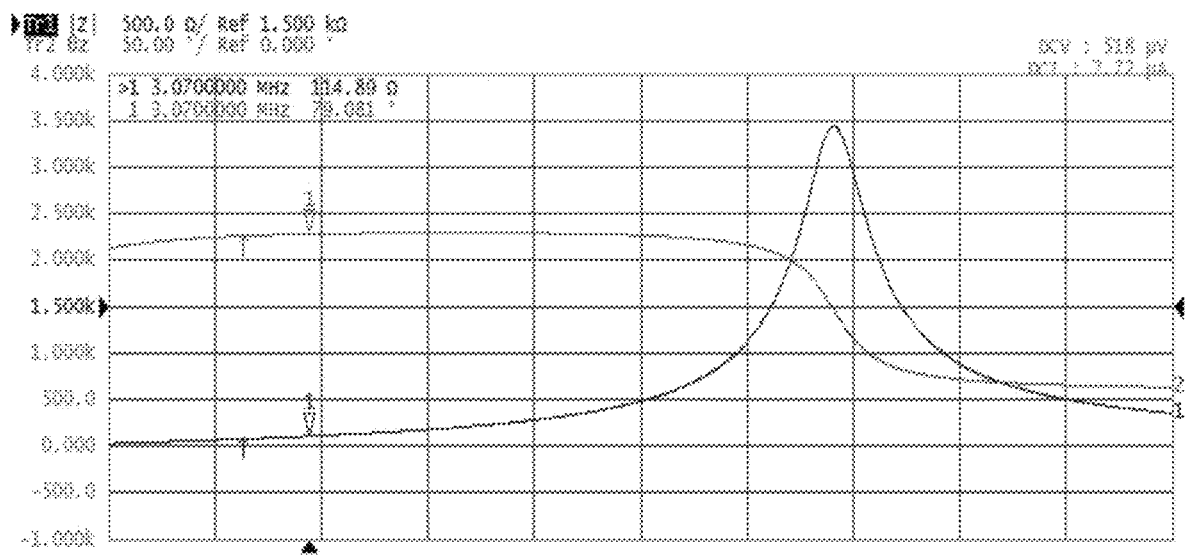
FIG. 4 is a graph of the frequency sweep data before and after the sensor is coupled to the receiver coil, where the yellow line represents the absolute impedance of the system and the blue line represent the phase shift.

Two identical coils both with 0.016 mm wire thickness, 0.016 mm wire gap, 50 turns with 25 turns on each side of the polyimide flex PCB were brought together within 1.2 mm distance separated by a 0.9 mm thick polystyrene plastic well bottom of a standard 96 well plate. Power was supplied to the receiver coil by the impedance analyzer at 50 µA current level at frequencies ranging from 1 MHz to 12 MHz. FIG. 3 shows the COMSOL simulation of the magnetic coupling of the two coils. The frequency sweep was performed with the impedance analyzer at a resolution of 1600 points, the absolute impedance and phase shift of the system were recorded before and after the sensor was brought within the coupling range of the two coils, as seen in FIG. 4. The result shows that the polystyrene 96 well plate is magnetically transparent enough to have negligible effect on the coupling of the two coils.

Construction of the Sensor System

Bacterial cultures were diluted and aliquoted into a standard 96 well plate with a sensor inserted in each well. A receiver coil connected to a Keysight E4990A-20 impedance analyzer on the bottom of the 96 well plates wirelessly communicate with the sensor and scans a spectrum of electrical wavelength to identify the resonance frequency between the sensor and the receiver coil. The resonance frequency of the system was recorded every 5 mins, combined with the parameter of the sensor to calculate the permittivity of the bacterial culture. The permittivity readout is plotted as a time series, and the slope of the curve over the initial 30 mins was used to access the sensitivity score of bacteria to each tested antibiotic. The baseline of the sensitivity score is determined by acquiring the time sequence slope in sterile LB medium without treatment and known sensitive strain.

All experiments were performed with cultures incubated at 30° C. and inoculation $OD_{600}$ of 0.001 unless noted otherwise. The positive and negative ends of the receiver coil situated in a die-cast aluminum electromagnetic insulated box is connected to the Impedance Analyzer via a pair of twisted and insulated stranded copper wire. The sensor was first mounted onto double-sided adhesive sheet and had the single layer protective polyurethane spray coating applied. The entire sheet of coated sensors was then left in a desiccator for 48 hours to ensure complete evaporation of solvent and curing of the coating material. Individual sensors were then removed from the sheet with adhesive backing, in turn rolled up as cup sleeves and placed inside of the wells, to avoid interference from protein and bacteria settling effect in a static culture environment, the sensing component of the sensor is placed vertical to the bottom of the well lining the wall of the well. Finally, the entire 96 well plate was placed in a UV Clave ultraviolet sterilization chamber for a 1-hour sterilization cycle. Three sensors were randomly selected to establish a baseline for each batch of sensors to ensure successful coating. On the Impedance Analyzer platform, a MATLAB program is used to trigger the equipment every 5 mins for a 35 mins duration, the program then takes the readout, search for the resonance frequency, and saved as time series for further analysis. The file triggered by the MATLAB program is written in VBScript to interface with the Impedance Analyzer to perform a preset 1600 points sweep within a 1 MHz range near the initial resonance frequency.

Sensor Design

Initial iteration of the sensor design composed of a fiber glass printed circuit board with 5 turns of coil on both sides of the PCB with 11 0.5 mm digits spaced 0.5 mm apart. The sensor was placed inside of a upside down 50 ml conical tubing with 20 mL of LB inoculated with 0.0001 OD600 *E. coli* MG1655 ASV. The assembly is then placed on a shaker set to 200 rpm overnight in a 37° C. culture room. The growth curve against background curve obtained from the system is shown in FIG. 7, the curve displays lag phage, exponential growth phase, and stationary phage. However, the slower detection speed of the sensor was unsatisfactory, which motivated a redesign of the sensor design aiming to achieve faster detection speed.

After performing analysis of the equation with method of Morris sensitivity analysis in SALib (Sensitivity Analysis Library in Python), it was revealed that the number of turns in the coil had the largest influence on the permittivity value, followed by the outer diameter of the coil and the distance D between the digits as seen in FIG. 8. This was taken into consideration when designing the sensors to achieve the highest sensitivity. After several iterations of sensor design, the final design of the sensor mentioned in the method section shows the highest sensitivity with rapid detection capability.

Bacterial Growth Monitoring and ASTs

To ensure the conductive nature of the media doesn't interfere with the sensor, low salt LB was selected as the medium for bacterial growth in this study. Growth curves for both regular LB and low salt LB were recorded with traditional OD600 measurement over a period of 12 hours (FIG. 9). Baseline readout of sterile medium was established and subsequently subtracted as background from the experimental data below. Initial growth monitoring was tested with $E.$ $coli$ MG1655, as seen in FIG. 10. Data revealed that compared to the growth curve based on $OD_{600}$, relative permittivity was more sensitive in detecting bacterial growth. Upon inoculation, there was an immediate increase in permittivity, likely due to nonspecific adsorption of proteins in growth medium onto the polyurethane coating. The protein adsorbed onto the sensor surface quickly saturates and forms a protein shell that is tens of nanometers thick, and this is observed in the sterile medium permittivity curve. Similar phenomena were observed when measuring the baseline, where there was an initial moderate increase in signal for sterile media alone. Further increase due to bacterial growth was recorded around 30 mins after inoculation, much earlier than OD600 measurement (around 5 h). The growth curve collected by the system showed logarithmic increase in relative permittivity which then slowed down over time and eventually reached a plateau. The presence of plateau is presumably due to the saturation of free space on the sensor surface by bacterial growth and associated products. Further experiments were done on two more different strains of both Gram-positive and Gram-negative bacteria to test if the functionality of the sensor extends beyond just $E.$ $coli$. As shown in FIG. 11, not only do all three strains elicit similar responses over the 3.5 hours monitoring period, the three strains show some segments of different patterns of growth, which can be investigated in future research for potential of strain identification using specific medium.

To determine if this sensor can be used for AST, an ampicillin sensitive strain $E.$ $coli$ MG1655 and ampicillin resistant strain $E.$ $coli$ MG1655 ASV were compared for growth in the absence and presence of ampicillin. Both strains were dosed with 100 µg/mL ampicillin at the time of inoculation and cultured for 4 hours, which is known to induce cell lysis in sensitive $E.$ $coli$ strains. As FIG. 12 shows, $E.$ $coli$ ASV strain grew in presence of ampicillin while the wildtype $E.$ $coli$ MG1655 strain was inhibited by the ampicillin treatment as expected, all of which was observed within 30 mins. The low initial increase in relative permittivity maybe from bacteria in the suspension being lysed, and the cellular content increased the permittivity near the sensor surface.

Subsequent experiments were performed on more antibiotics and all three previously tested bacterial species, with the detection window of sensitivity to antibiotics within 30 mins. In order to create a more uniform test time towards the goal of creating a standard method, the test time was set universally at 30 mins with 5 mins read interval, since most growth curves shows initial signs of resistance or growth in that time frame, as seen in FIG. 12. At the same time, to obtain more rapid detection of growth and distinguish resistant vs. sensitive strains, a linear regression was opted in on the relative permittivity on a logarithmic scale. The slopes of the best fit line were then used as a sensitivity score to determine the sensitivity of strains toward antibiotics. It can be seen in FIGS. 13-21 that the dose dependency nature of bacterial susceptibility to antibiotics can be seen in both LC sensor system and OD600 measurement, where trends of growth inhibition after 6-10 hours in OD600 measurement was captured by the slope of permittivity measurement substantially earlier in just 30 mins.

Performance in the Presence of Host Proteins

Samples collected in a clinical setting is often complex. Whole blood, plasma, serum, urine, or other liquid from the human body contains significantly more types and larger amounts of proteins and cells compared to a laboratory culture media. Thus, it is necessary to test the sensor system with the addition of complex components in order to determine the feasibility of implementing this system in clinical setting where sample preparation beyond dilution and centrifugation is seldom performed. For the above reasons, fetal bovine serum was selected to mimic human serum and added to low salt LB at different percentages. The response of the sensor system is shown in FIG. 22. Encouragingly, at lower concentrations, there is 1 sufficient free space near the surface of the sensor for sensing bacterial growth. For low salt LB dosed with 2% of FBS, the growth of $E.$ $coli$ wildtype strain MG1655?? was captured by the LC sensor system with little interference from the serum. This demonstrates the possibility of using these sensors in clinical settings. When the amount of PBS reached 5%, the response was lost, likely because the free space thickness was saturated by protein adsorption.

$$d_{sat} = -\frac{D}{a_1}\ln\left(\frac{0.005}{a_2}\right) \quad (8)$$

$$a_1 = 114.97(W+D)^3 + 28.75(W+D)^2 - 9.183(W+D) + 1.631 \quad (9)$$

$$a_2 = 1293.21(W+D)^3 + 164.87(W+D)^2 - 6.521(W+D) + 6.105 \quad (10)$$

With thicker free space for sensing, the system can be further optimized to capture more complex samples, and longer-term growth pattern.

This study demonstrated that the feasibility of rapid AST using LC sensor in a 96 well plate format. To our best knowledge, this is the fastest AST test at the phenotype level without using complex equipment. Compared to genotypic ASTs, this system only requires simple sample preparation (dilution only) and can be fitted into an automated workflow for high-throughput detection. The system can generate reports with little computational power without needing an advanced data analyst or the capability of handling massive data sets (e.g., those required by MALDI-TOF). The system is also not limited to the use of specific cartridges for a limited selection of strains, instead uses a reference library for identifying MIC of antibiotics of interest. Compared with other existing automated phenotypical approaches, this method achieves AST with significantly shorter detection time (~30 mins). The system can be optimized in the future by employing high-throughput method in which the whole 96 well-plate can be processed in a relatively short amount of time, enabling a more comprehensive assay. This is part of our ongoing work. The coating material and coating thickness of the chips can also be optimized to achieve higher accuracy and tolerance to fouling from the growth media or cellular products. The results of 2% FBS demonstrates the possibility to test clinical samples after simple dilution of patient sample. To handle even higher serum percentage, the IDE design could be adjusted to increase the saturation thickness ergo increase the upper concentration limit of FBS content. It has been reported that the saturation thickness can be described by Eq. 8-10, where a1 and a2 are both functions of digit width W and gap width D.

$$d_{sat} = -\frac{D}{a_1}\ln\left(\frac{0.005}{a_2}\right) \quad (8)$$

$$a_1 = 114.97(W+D)^3 + 28.75(W+D)^2 - 9.183(W+D) + 1.631 \quad (9)$$

$$a_2 = 1293.21(W+D)^3 + 164.87(W+D)^2 - 6.521(W+D) + 6.105 \quad (10)$$

With thicker free space for sensing, the system can be further optimized to capture more complex samples, and longer-term growth pattern. The design of the LC sensor too, can be modified and optimized to fit into various format. For example, lithography could be used to fit the system into smaller format or microfluidic devices.

What is claimed is:

1. A system for performing a rapid antimicrobial susceptibility test, comprising:
   a well including a cavity for receiving a sample containing a microbial population and an antimicrobial;
   a sensor having a set of defined parameters positioned vertically in the well so that the sensor will contact the sample;
   a receiver positioned under the well and wirelessly coupled to the sensor; and
   an impedance analyzer connected to the receiver and configured to identify a resonance frequency of the sensor and the receiver, to record the resonance frequency over a predetermined set of first time periods, to calculate the permittivity of the sample based on the resonance frequency and the defined parameters of the sensor, and to track the permittivity over a second predetermined time period.

2. The system of claim 1, wherein the sensor comprises an interdigitated capacitor.

3. The system of claim 2, wherein the defined parameters comprise a number of digits, a length of each digit, a distance of a gap between each digit, and a width of each digit.

4. The system of claim 3, wherein the receiver comprises a detection coil and an electro impedance spectrometer.

5. The system of claim 4, wherein each first time period of the predetermined set of first time periods comprises five minutes.

6. The system of claim 5, wherein the second predetermined time period is thirty minutes.

7. The system of claim 6, further comprising a well plate including the well.

8. The system of claim 7, wherein the well plate includes a plurality of additional wells, wherein each additional well include an additional sensor positioned vertically in the additional well that is wirelessly coupled to an additional receiver positioned under the additional well.

9. The system of claim 1, wherein the microbial population in a bacterial population and the antimicrobial is an antibiotic.

10. A method of performing an antimicrobial susceptibility test, comprising the steps of:
    providing a well including a cavity, a sensor having a set of defined parameters positioned in the well, and a receiver positioned under the well and wirelessly coupled to the sensor;
    adding a sample containing a microbial population and an antimicrobial to the well so that the sample contacts the sensors;
    using an impedance analyzer connected to the receiver to identify a resonance frequency of the sensor and the receiver;
    recording the resonance frequency over a predetermined set of first time periods;
    calculating the permittivity of the sample based on the resonance frequency and the defined parameters of the sensor; and
    tracking the calculated permittivity over a second predetermined time period.

11. The method of claim 10, further comprising the step of plotting the calculated permittivity over the second time period.

12. The method of claim 11, further comprising the step of determining whether the bacterial population is susceptible to the antibiotic based on the slope of the plotted permittivity over the second time period.

13. The method of claim 12, wherein the sensor comprises an interdigitated capacitor.

14. The method of claim 13, wherein the step of calculating the permittivity of the sample uses the resonance frequency and the defined parameters of the sensor.

15. The method of claim 14, wherein the defined parameters comprise a number of digits, a length of each digit, a distance of a gap between each digit, and a width of each digit.

16. The method of claim 15, wherein the receiver comprises a detection coil and an electro impedance spectrometer.

17. The method of claim 16, wherein each first time period of the predetermined set of first time periods comprises five minutes.

18. The method of claim 17, wherein the second predetermined time period is thirty minutes.

19. The method of claim 18, wherein the step of providing a well includes providing a well plate including the well and a plurality of additional wells, wherein each additional well includes an additional sensor positioned in the additional well that is wireless coupled to an additional receiver positioned under the additional well.

20. The method of claim 10, wherein the microbial population in a bacterial population and the antimicrobial is an antibiotic.

* * * * *